United States Patent [19]

Ayers et al.

[11] 4,224,439
[45] Sep. 23, 1980

[54] ACTIVATED MATRIX AND METHOD OF ACTIVATION

[75] Inventors: John S. Ayers; Geoffrey S. Bethell; William S. Hancock, all of Palmerston North; Milton T. W. Hearn, Dunedin North, all of

[73] Assignee: Development Finance Corporation of New Zealand, Wellington, New Zealand

[21] Appl. No.: 874,628

[22] Filed: Feb. 2, 1978

[30] Foreign Application Priority Data

Feb. 8, 1977 [NZ] New Zealand .......................... 183283

[51] Int. Cl.$^2$ ................................................ C08B 3/00
[52] U.S. Cl. .................... 536/32; 260/112 R; 260/112.5 R; 260/6; 536/43; 536/44; 536/48; 536/49; 536/50; 536/107; 536/108; 536/110; 536/115
[58] Field of Search .................... 536/32, 43, 44, 48, 536/49, 50, 107, 108, 110, 115, 120, 112 R; 260/112.5 R, 6

[56] References Cited

U.S. PATENT DOCUMENTS

| | | | |
|---|---|---|---|
| 3,271,387 | 9/1966 | Patel et al. | 536/107 |
| 3,376,287 | 4/1968 | Jarowenko et al. | 536/107 |
| 3,793,065 | 2/1974 | Morrison et al. | 536/110 |
| 3,833,555 | 9/1974 | Keys et al. | 536/48 |
| 3,880,832 | 4/1975 | Tessler | 536/50 |
| 4,020,268 | 4/1977 | Nishikawa et al. | 536/43 |

FOREIGN PATENT DOCUMENTS

| | | |
|---|---|---|
| 997051 | 6/1965 | United Kingdom . |
| 1022810 | 3/1966 | United Kingdom . |
| 1084476 | 9/1967 | United Kingdom . |
| 1186740 | 4/1970 | United Kingdom . |
| 1190000 | 4/1970 | United Kingdom . |
| 1289549 | 9/1972 | United Kingdom . |

*Primary Examiner*—Melvyn I. Marquis
*Attorney, Agent, or Firm*—Holman & Stern

[57] ABSTRACT

Carbonylation of a polysaccharide and the product of that carbonylation. The carbonylated product can be used to prepare an affinity chromatography matrix which is an uncharged species of varying pH's. The carbonylated product is also useful for the preparation of other compounds. Typical polysaccharides are agarose, starch, dextran, cellulose and regenerated cellulose and typical carbonylating agents are N,N'-carbonyl diimidazole; N,N' carbonyl di-1,2,3-benzotriazole; and N,N'-carbonyl di-1,2,4-triazole.

15 Claims, 4 Drawing Figures

ACTIVATED MATRIX AND METHOD OF ACTIVATION

BACKGROUND OF THE INVENTION

1. Field of the Invention

This invention relates to an activated matrix and to a method of activating the matrix. It further relates to the activated matrix further coupled to a ligand or leash and to a method of coupling the ligand or leash.

For the purposes of this specification, activating a matrix means carbonylating a polysaccharide with a suitable carbonylating agent. Activated matrix means a product of such a carbonylating reaction. Coupling a ligand or leash means substituting a ligand or leash having a good nucleophilic group, such as an active amino group, into the carbonyl group of the activated matrix. A ligand is a substituent selected to be specifically attractive to a compound sought to be bound to the coupled matrix. Such binding may be by ion exchange, affinity chromatography, for a radioimmune assay, for hydrophobic chromatrography or as an enzyme support or the like. A leash is a substituent which can be readily substituted into the carbonyl group of the activated matrix and then itself be substituted by a ligand.

2. Discussion of the Prior Art

Affinity chromatography is a separation technique exploiting the unique specificity of biological interaction to isolate naturally occurring compounds such as proteins, polysaccharides, glycoproteins and nucleic acids. Specific adsorptive properties are imparted to a bed material by covalently bonding an appropriate binding ligand to an insoluble matrix, i.e. by activating the matrix. The ligand acts to adsorb from solution a substance to be isolated, the isolated substance subsequently being dissolved by changing the experimental conditions after unbound substances have been washed away. The high specificities exploited by this method are natural specificities such as, for example, antigen-/antibody, enzyme/inhibitor or hormone/carrier. Isolation of substances through this technique differs from conventional chromatography in which separation depends on gross physical and chemical differences between the substances.

Affinity chromatographic matrices are prepared by first activating a polysaccharide and then coupling a ligand and leash when required. In one such preparation agarose is reacted in a two-stage process as set out below. The first stage comprises treatment with cyanogen bromide to form an imido-carbonate compound of Formula I and the second stage comprises treatment with a primary amine to form an isourea compound of Formula II as set out hereinbelow:

wherein R is a suitable affinity chromatography ligand. In the second stage reaction involving a nitrogen nucleophile the matrix becomes, in part, an ion exchange resin charged with the basic isourea group. This charge is present at pH 7 thus interfering with the specificity of the compound when attempting to isolate substances from animal bodily fluids. It also remains, but to a lesser extent, at higher pH levels. It will be appreciated that the specificity of the ligand would be considerably reduced by the presence of the charged groups thus reducing the desirability of the matrix activated by this method.

SUMMARY OF THE INVENTION

It is an object of one aspect of this invention to go some way toward overcoming this disadvantage or to at least provide the public with a useful choice.

It has also been found that a matrix activated according to one aspect of this invention has a higher concentration of activating groups than that obtained by activation by the cyanogen bromide method. This makes the activated matrix of this invention very attractive regardless of whether it is used directly, for example as an enzyme support, or coupled with a ligand or leash.

Accordingly the invention may be said broadly to consist in a compound of the general formula III:

wherein the matrix is a water and organic solvent insoluble polysaccharide matrix and Y is a good leaving group which is readily displaced by an amine.

Preferably the matrix is cross-linked agarose, cross-linked starch, cross-linked dextran, cross-linked cellulose or regenerated cellulose or cross-linked hydroxy $C_2$–$C_4$ alkylated cellulose or regenerated cellulose and Y is imidazoyl; 1,2,4-triazoyl; 1,2,3-benzotriazoyl, chloride, or some other good leaving group.

In another aspect, the invention may be said broadly to consist in the method of preparing a compound of Formula III:

wherein the matrix is a water and organic insoluble polysaccharide matrix and Y is either a good leaving group which is readily displaced by an amine or a substituent whose C-Y bond is readily cleaved, which process comprises carbonylating a water and organic solvent insoluble polysaccaride matrix with a carbonylating agent of the general formula:

wherein Y is as defined above and X is either the same as Y or another suitable leaving group which combines with a hydrogen atom during said carbonylation.

Preferably the carbonylating reagent is N,N'-carbonyl diimidazole; N,N'-carbonyl di-1,2,3-benzotriazole; or N,N'-carbonyl di-1,2,4-triazole.

Preferably the matrix is cross-linked agarose, cross-linked starch, cross-linked dextran, cross-linked cellulose or regenerated cellulose, or cross-linked hydroxy $C_2$–$C_4$ alkylated cellulose or regenerated cellulose.

When the carbonylating agent is N,N'-carbonyl di-1,2,4-triazole or N,N'-carbonyl diimidazole the reaction is preferably conducted in a suitable organic solvent for at least five minutes at a temperature from 0° C. to 80° C., the upper limit being dependent upon the temperature at which the matrix begins to degrade.

In a still further embodiment the invention may be said broadly to consist in a compound of the general formula V:

$$\text{MATRIX} - \text{O} - \underset{\underset{\text{O}}{\|}}{\text{C}} - \text{NR}^1\text{R}^2 \qquad V$$

wherein the matrix is as defined above when $R^1$ or $R^2$ may be hydrogen or an alkyl group and the other is ligand (as hereinbefore defined) or a leash (as hereinbefore defined).

Preferably $R^1$ or $R^2$ is $-(CH_2)_nNH_2$, $-(CH_2)_nNHR^3$, $-(CH_2)_nCOR^4$, or $-(CH_2)_nCO_2H$, wherein n is an integer from 2 to 12 and $R^3$ and $R^4$, which may be the same or different, are remainders of organic compounds. Alternatively $R^1$ and $R^2$ may be remainders of a peptide, protein, steroid, amino acid or carbohydrate.

In yet another embodiment, the invention may be said broadly to consist in a method of preparing a compound of general formula V which comprises reacting a compound of the general formula $NHR^1R^2$ wherein $R^1$ and $R^2$ are as defined hereinabove, with a compound of general formula III as defined hereinabove.

BRIEF DESCRIPTION OF THE DRAWINGS

The invention may be more fully understood by having reference to the following drawings, wherein.

The figures will be referred to later during the discussion of the following examples.

EXAMPLES

1. ACTIVATION OF SEPHAROSE CL-6B MATRIX WITH CDI

SEPHAROSE CL-6B (a trade mark of Pharmacia Fine Chemicals for cross-linked agarose), 3 g Moist cake was washed sequentially with water, dioxan-water 3:7, dioxan-water 7:3 and dioxan (50 ml of each) and was suspended in dioxan (5 ml). 1,1-Carbonyl diimidazole (CDI) (0.12 g) was added, and the suspension shaken at room temperature. It was washed with dioxan (100 ml) and used immediately. Duplicate experiments were carried out for times varying between 0.25 and 6 hr. and the products were analysed as described below.

2. ACTIVATION OF DIFFERENT MATRICES WITH CDI (a) CROSS-LINKING CELLULOSE AND REGENERATED CELLULOSE

WHATMAN CC-31 cellulose (a trade mark of W & R Balston Ltd.) (10 g) was reacted with 1 ml of epichlorohydrin in 30% NaOH solution at 65° C. for two hours. ENKA regenerated cellulose (10 g) was reacted in the same way.

(b) HYDROXYPROPYLATING CROSS-LINKED CELLULOSE AND REGENERATED CELLULOSE

Cellulose and regenerated cellulose as in 2(a) were treated under identical conditions except that the reaction vessel was sealed, 0.2 ml and 1 ml of epichlorohydrin were used for the regenerated cellulose and cellulose respectively and 5 ml of propylene oxide was added in both cases.

(c) ACTIVATION

SEPHAROSE CL-6B and the products of Examples 2(a) and 2(b) were activated in a manner similar to that in Example 1. Reagents and yields are set out in Table 1.

TABLE 1

| MATRIX | Wt(g) | Amount of CDI (mmoles) | Reaction time(h) | Solvent | m moles | Yield % based on reagent |
|---|---|---|---|---|---|---|
| SEPHAROSE CL-6B | 3[1] | 0.93 | 0.25 | dioxan | 0.400 | 43 |
| SEPHAROSE CL-6B | 3[1] | 2.07 | 2 | dioxan | 0.875 | 42 |
| Whatman Cellulose [3] | 0.2 | 0.93 | 0.5 | DMF[4] | 0.080 | 8.6 |
| Cellulose [3,5] Modified | 0.2 | 0.93 | 0.5 | DMF[4] | 0.074 | 7.7 |
| Cellulose [2,6] modified | 0.2 | 0.93 | 0.5 | DMF[4] | 0.436 | 47 |
| cellulose [2,7] modified regenerated | 0.2 | 0.93 | 0.5 | DMF[4] | 0.636 | 69 |

TABLE 1-continued

| MATRIX | Wt(g) | Amount of CDI (mmoles) | Reaction time(h) | Solvent | m moles | Yield % based on reagent |
|---|---|---|---|---|---|---|
| cellulose [5,8] | 0.2 | 0.93 | 0.5 | DMF[4] | 0.644 | 69 |

[1]Weight of moist cake,
[2]Methanol dried,
[3]Whatman microgranular cellulose CC-31
[4]Presoaked overnight,
[5]Freeze dried
6 Cellulose CC-31 (10g) after reaction with epichlorhydrin (1ml) in 30% NaOH
[7]Same product as 6 except that 5ml of propylene oxide was also added.
[8]Derived from ENKA regenerated cellulose (10g) with 0.2ml of epichlorhydrin, 5ml propylene oxide in 30% NaOH.

Figure 4:
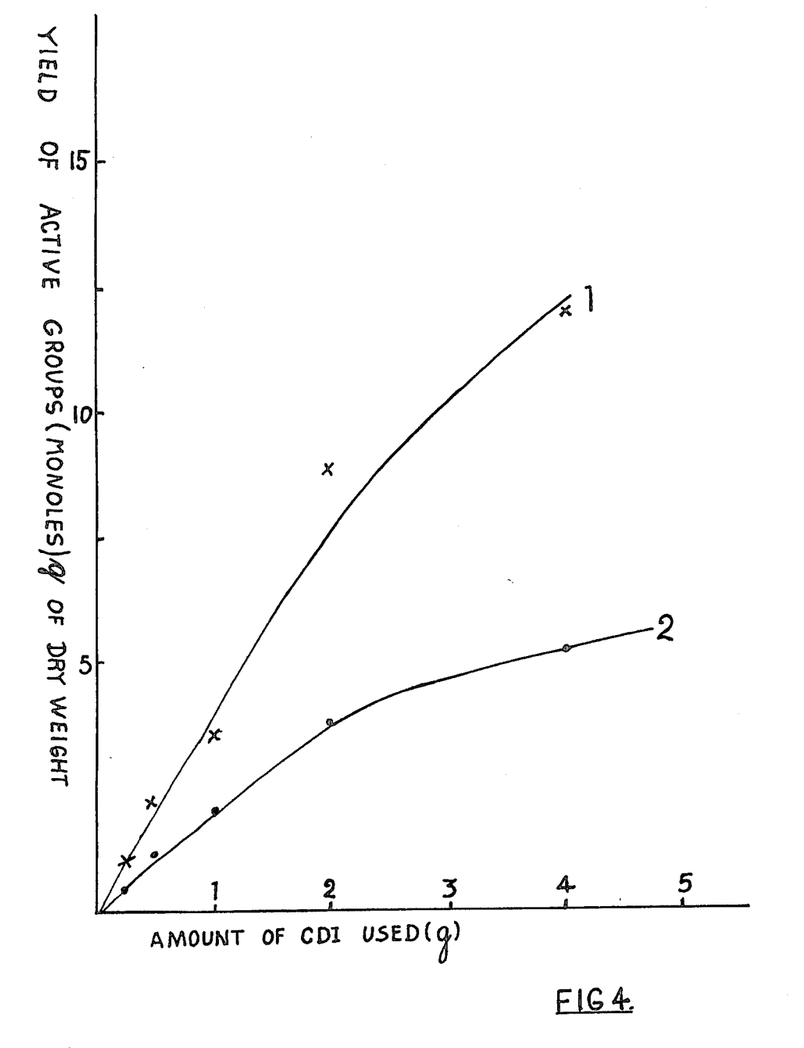
FIG. 4 shows comparative plots of yields of active groups with varying matrices. Curve 1 is the yield when cross-linked hydroxypropylated regenerated cellulose is the matrix and the curve 2 is the yield for cross-linked agarose.

It will also be seen from FIG. 4 that the yield of hydroxypropylated cross-linked regenerated cellulose is greater than that of SEPHAROSE CL-6B when each is activated with CDI.

3. COUPLING OF LIGANDS OR LEASHES TO ACTIVATED MATRIX (a) The material from example 1 was treated at 4° C. overnight with η-butylamine, (1.4 g) in water (9 ml) at pH 10 and was washed sequentially with water (200 ml), 1 M NaCl (100 ml) and water (200 ml). Materials for titration were further washed with 0.005 M HCl (200 ml).

(b) The coupling as described in Example 3(a) was repeated using a 1,6 diaminohexane. Materials for titration were as before.

(c) Similarly an activated matrix from example 1 was coupled with 6-amino hexanoic acid.

(d) Coupling of ethanolamine to 6-aminohexanoic acid SEPHAROSE

The coupled SEPHAROSE CL-6B from Example 3(c) (3 g moist cake) was treated with ethanolamine (0.5 g) and 1-cyclohexyl-3-(2-morpholinoethyl)-metho-p-toluene sulphonate (CMC) (0.5 g) at pH 6 overnight at room temperature. The material was washed as for the coupling step.

(e) Cross-linked agarose (3 g moist cake), CDI (333 mg), 2 hour activation gave 875 μmoles of active groups (by titration, coupled with 1.4 g of 6-aminohexanoic acid at pH 10 (left 12h) and gave 390 μmoles of titratible carboxyl groups (pK 4.7). This gave a capacity of 1.95 mmoles/g of dry weight.

4. ANALYSIS OF ACTIVATED MATRIX

The activated matrices (0.2 g) from Example 1 and 2(c) were hydrolysed overnight at room temperature in 0.15 M NaOH (50 ml). 20 ml portions of the supernatant liquid were then titrated under nitrogen for carbonate in the presence of hydroxide ions. The solutions were retitrated over the same pH range, after all the carbon dioxide had been expelled by flushing with nitrogen at pH 2.5. The second figure gave the imidazoyl content of the sample. The difference between the two figures gave the carbonate content of the sample.

A sample of the same activated matrix was found to have 6.92 and 6.99% nitrogen by elemental analysis. Calculated on the basis of the above titration figure the expected value for N was 6.48%.

Coupled matrices (0.2 g dry weight) from Examples 3a to 3e were titrated potentiometrically under nitrogen using 2 M KOH (1 μl aliquots) under nitrogen from pH 3–11.7 in a total of 8 ml H₂O. Titrations were performed using a Radiometer TTT2 automatic titration assembly.

5. COMPARISON WITH CNBr ACTIVATED SEPHAROSE

In order to compare the linkage in an affinity matrix from CDI activated SEPHAROSE with that from cyanogen bromide activated SEPHAROSE, {prepared by the method described in Analytical Biochemistry 60, 149–152 (1974)}, η-butylamine was coupled to each activated SEPHAROSE.

Figure 1:
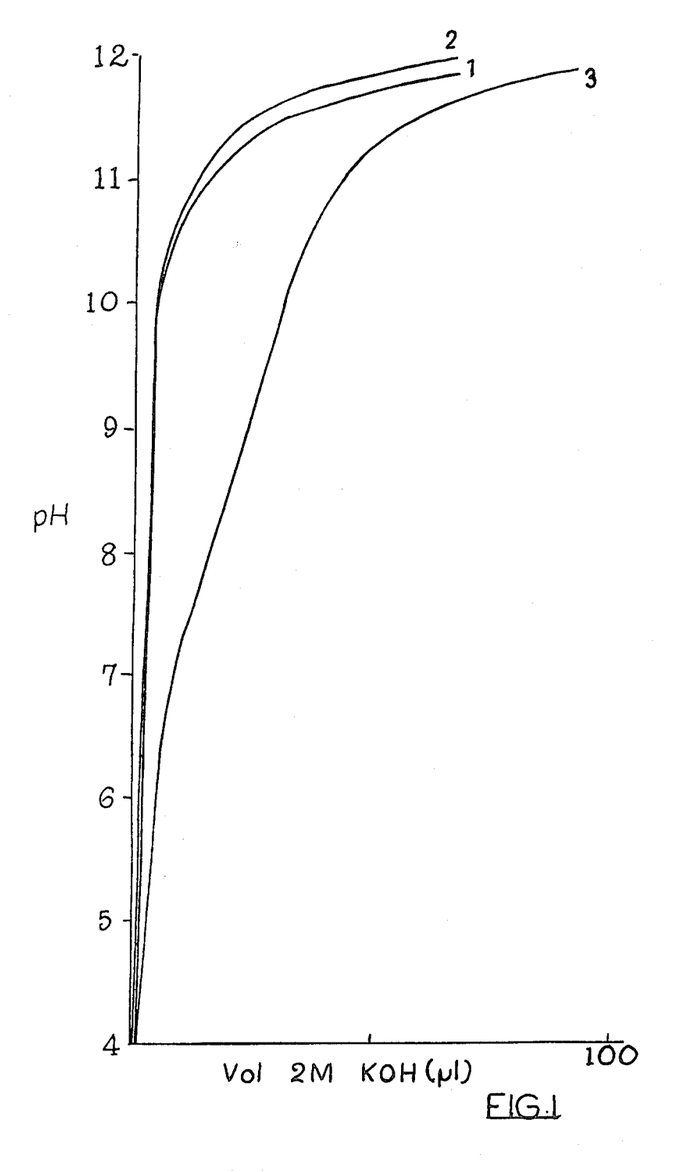
FIG. 1 shows titration curves of η-butylamine-SEPHAROSE in $H_2O$, curve 1 being SEPHAROSE CL-6B alone, curve 2 being η-butylamine-SEPHAROSE CL-6B coupled by the CDI method and curve 3 being η-butylamine-Sepharose CL-6B coupled by the cyanogen bromide method.

The titration curves for the two coupled activated matrices as well as the control with unactivated SEPHAROSE alone are shown in FIG. 1. It will be seen that the titration curve of η-butylamine-SEPHAROSE (CDI method) was virtually identical to that of the untreated SEPHAROSE. That of η-butylamine-SEPHAROSE (cyanogen bromide method) clearly indicated the presence of charged groups ($pK_a$ 8, 240 μmoles per dry g) usually considered to be isoureas.

Figure 2:
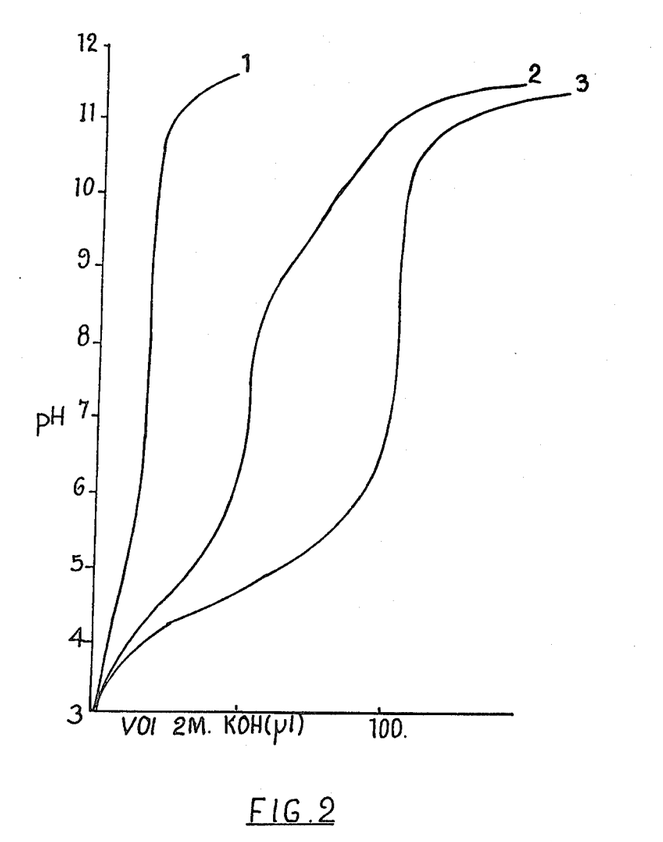
FIG. 2 shows titration curves of 6-amino hexanoic acid SEPHAROSE in 0.5 M NaCl. Curve 1 is 6-amino hexanoic acid-SEPHAROSE CL-6B coupled by the CDI method (103 micromoles-g), curve 2 is 6-amino hexanoic acid-SEPHAROSE CL-6B coupled by the cyanogen bromide method and plot 3 being 6-amino hexanoic acid-SEPHAROSE CL-6B coupled by the CDI method (825 micromoles-g).
Figure 3:
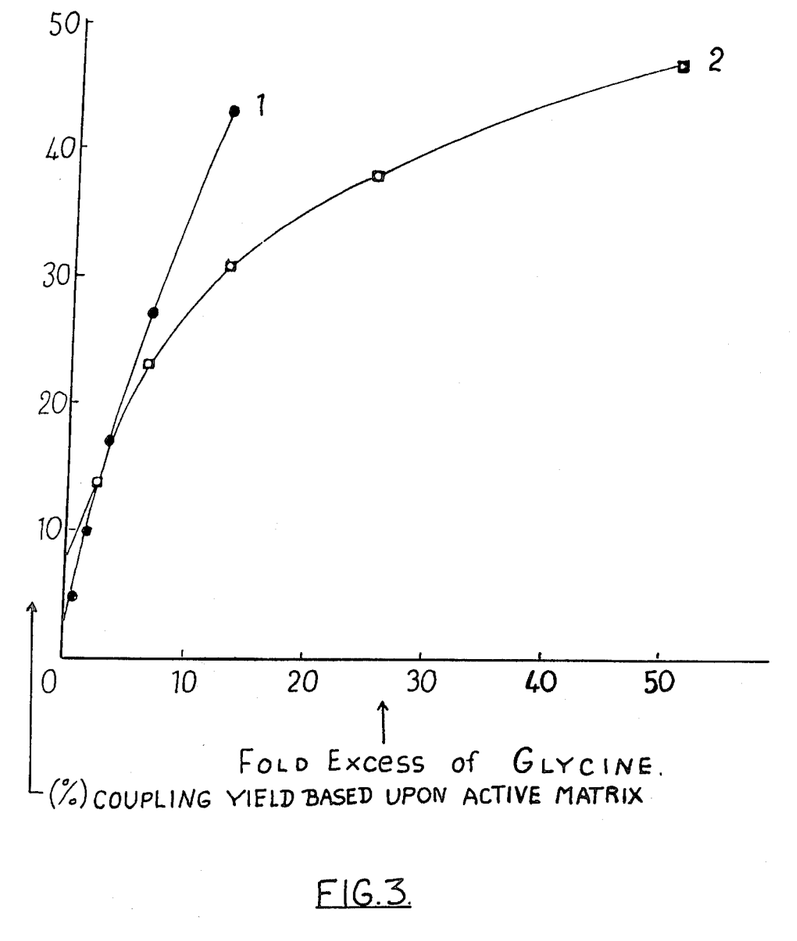
FIG. 3 shows comparative plots of coupling yields of glycine. Curve 1 is a CDI activated matrix while curve 2 is a CNBr activated matrix.

6-Aminohexanoic acid-SEPHAROSES were then prepared by each method and examined by titration to show that amines did indeed couple by this new method. The titration curves comparing these two products are shown in FIG. 2. The titration curves indicated the presence of carboxyl groups ($pk_a$ 4.7, 103 and 825 μmoles per dry g) but the curve was identical to that of untreated SEPHAROSE CL-6B at alkaline pH's. On the other hand the titration curve of 6-aminohexanoic acid-SEPHAROSE (cyanogen bromide method) indicated the presence of two charged groups ($pk_a$ 4.7, carboxyl, 390 μmoles per dry g, and $pk_a$ 9.5, isourea) in an approximate ratio of 1.2;1.0. This is close to the expected value of 1:1 if an isourea group is formed on attachment of each molecule of the acid.

The 6-aminohexanoic acid-SEPHAROSE (CDI method) was then blocked with ethanolamine by means of a water soluble carbodiimide and a further titration curve was run. This indicated an absence of charged groups in the pH range 3–10 demonstrating that a leash and a ligand can be attached by this method without introducing additional charged groups or leaving unblocked carboxyl functions.

These experiments show that no charged groups are introduced on to SEPHAROSE CL-6B by activation with 1,1'-carbonyl diimidazole and subsequent treatment with simple amines.

6. COMPARISON OF ACTIVATING REAGENTS

The following activation reagents were tried:
(a) N,N' carbonyl diimidazole (CDI) in dioxan
(b) N,N' carbonyl di-1,2,4-triazole (CDT) in dioxan
(c) N,N' carbonyl di-1,2,3-benzotriazole (CDB) in dioxan
(d) Phosgene in dioxan (phosgene)

(e) Cyanogen bromide in 1 M sodium carbonate followed by hydrolysis in 1 M HCl for 0.5 h (CNBr/HCl).

(f) Cyanogen bromide in 1 M sodium carbonate for comparison purposes (CNBr).

The following results (Table 2) were obtained on a 3 g moist cake of SEPHAROSE in 5-6 ml dioxan or 12 ml 1 M Na₂CO₃ as appropriate.

TABLE 2

| Method | Reaction Time | mmoles reagent used | Activation yield (μmoles/sample) | % yield based on reagent |
|---|---|---|---|---|
| CDI | 15 min | 0.93 | 400 | 43 |
| CDT | 15 min | 0.93 | 315 | 35 |
| CDB | 7 days | 0.63 | 80 | 12.7 |
| Phosgene | 30 min | 4.45 | 310 | 7 |
| CNBr | 4 min | ~6 | 105 | 2 |
| CNBr/HCl | 4 min plus 30 min | ~6 | 105 | 2 |

For the first four reagents, activation yields were obtained by hydrolysing the dioxan washed product in 0.15 M alkali overnight at room temperature and then titrating the supernatent liquid for carbonate ions. Yields for the CNBr reagent were based on the Kjeldahl nitrogen determination thus:

Hence the difference in nitrogen content on the matrix before and after hydrolysis with 1 M HCl gave the number of active imidocarbonate groups formed. This figure also gave the number of active cyclic carbonate groups produced by this hydrolysis. A sample of the acid hydrolysed product was also analysed by the carbonate titration method above and gave a figure of 150 μmoles sample. This is higher than the Kjeldahl figure, not surprisingly, since the slow reaction:

also takes place and therefore some of the inactive carbamate groups are also "counted".

The reactions between SEPHAROSE and CDI and CDT could be left until it was convenient to do the work up, activation yields being identical for reaction times of between 0.25 and 6 hours. This is in direct contrast to the CNBr method which requires the work up to be done as quickly as possible. In addition, the activation yield could be greatly increased if more CDI were used whereas with the CNBr method, only a further 10% of active groups were present even if the amount of reagent was quadrupled.

CDB was used to activate SEPHAROSE but the reaction was very slow. Even after 7 days, yields were only 80 μmoles and only 13% of the reagent had been consumed. This was probably due to a steric effect. As in the case of CDI, the active species was found to be acyclic. Benzotriazole was found by titration analysis.

The activation of SEPHAROSE with phosgene was carried out with a large excess of phosgene used for shorter reaction times.

Cyclic carbonates were formed on SEPHAROSE by the known procedure of hydrolysing in acid solution an imidocarbonate formed by the CNBr method. Treatment of the imidocarbonate with 1 M HCl for 0.5 h gave a product which averaged 105 μmoles of groups per 3 g of wet resin. A similar hydrolysis with 0.001 M acid gave 92 μmoles of cyclic carbonates. 1 M acid was generally used as it was found not to significantly degrade the matrix, even during 0.5 h reaction times.

7. DETERMINATION OF COUPLING TIMES

The activated matrices above were subjected to hydrolysis at various pH's. These reactions were monitored by measuring the amount of alkali (or acid in the case of pH 5) required to maintain the required pH as a function of time. The reactions were found not to be first order in that successive half-lives tended to increase. Table 3 shows the total times for each reaction carried out at room temperature.

TABLE 3

| Activation Method | Reaction Time (hrs) | | | |
|---|---|---|---|---|
| | pH 5 | pH 8½-9 | pH 10 | pH 11 |
| CDI | 20 | 30 | 10 | 1.5 |
| CDT | — | 4 | 1.5 | — |
| CDB | — | 1 | 1 | — |

These figures give a measure of the length of time for which any coupling reaction should be left in order to completely remove all active groups. As a result of this, reactions with the CDI activated matrix were generally left overnight at pH 10 and over the weekend at pH 9, or treated with an excess of ethanolamine to block unreacted active groups. The greater stability of the CDI relative to the CNBr activated matrix simplifies its filtration and washing before addition of the ligand or leash.

The CDT activated matrix was much more reactive than the CDI matrix and could be used where rapid coupling reactions are required.

8. COMPARISON OF COUPLING YIELDS

A series of couplings of three amines of differing pK values were carried out to find out the comparative reactivities towards amines and water of the active groups on each matrix. The amines selected were 6-aminohexanoic acid (pKa ~11), glycine (pKa 9.8) and glycylglycine (pKa 8.1). In addition 1,6-diaminohexane (pKa ~11) was tried in one case. The amines were present in large excess (5.4 mmoles) and were maintained at the required pH either by pH statting or by buffering using 1 M carbonate at pH 10 or 1 M N,N,N',N'-tetramethylethylene diamine at pH 9. At pH 11 6-aminohexanoic acid was used without additional buffer. The results are tabulated in Table 4.

TABLE 4

| Method | Active groups (μmoles/sample) | 6-aminohexanoic acid PH | | | 1,6-diaminohexane PH | Dioxan Solution | Glycine PH | | Glycyglycine PH | |
|---|---|---|---|---|---|---|---|---|---|---|
| | | 9 | 10 | 11 | 10 | | 9 | 10 | 9 | 10 |
| CDI | 400* | 64 | 130 | 162 | 130 | 280 | 122 | 194 | 224 | 80 |
| CDT | 315 | 86 | 155 | — | — | — | 149 | 198 | 154 | 70 |
| CBD | 70 | — | 43 | — | — | — | — | — | — | — |
| Phosgene | 80 | — | 28+ | — | — | — | — | 38 | — | 20 |
| CNBr | 105 | 64 | 65 | — | — | — | 49 | 50 | 34 | 30 |
| CNBr/HCl | 105 | 31 | 44 | — | — | — | 30 | 39 | 30 | 14 |

*washed with water prior to reaction
+A figure of 174 was obtained for 6-aminohexanoic acid at pH 10 when the activation was left for 2½ days. The figures were obtained by titrations of the end groups on the matrix with standard alkali.

For a given amine under the same conditions, the percentage coupling yields of each activated matrix are very similar. For example, generally for 6-aminohexanoic acid at pH 10 each activated matrix has 45–60% of its active groups available for coupling. Each amine appears to couple best at a pH which is about 1 unit above its pKa value. This is the point at which an increase in pH will not increase the free amine concentration but will increase the concentration of hydroxide ions and hence the hydrolysis rate. Conversely a decrease in pH, whilst it will decrease the hydroxide ion concentration, will also decrease the concentration of the free amine, more of it existing as the protonated form.

Summarising therefore, on the grounds of cost and capacity the CDT and CDB activated matrices would not appear to offer any advantages over the cheaper CDI method except that the CDT method offers a greater rate of coupling. The CDI method would seem to be comparable with the standard CNBr method with the added advantage of being more pleasant to handle. The phosgene method also shows some potential for coupling amines but as this is just as unpleasant to handle as the CNBr method its use might be limited to industry where the low cost of the reagent would doubtless be appreciated.

There is little doubt however that the greatest advantage of the methods based on the carbonyl reagents over the CNBr method lies in the fact that no charged groups are introduced on to the matrix during the coupling step.

9. USE OF ACTIVATED MATRIX AS TRYPSIN AFFINITY SUPPORT

Preparation of trypsin affinity supports (a) The activated SEPHAROSE CL-6B (from 3 g moist cake and 50 mg CDI) was treated overnight at 4° C. with 6-aminohexanoic acid (0.7 g) in H₂O (9 ml) at pH 10. It was then washed as in Example 3a. Two 1 ml portions of this material were treated at pH 4.7 for 24 hours at room temperature with CMC (0.12 g) and p-aminobenzamidine hydrochloride (5 or 10 mg) and subjected to the same washing procedure.

(b) Soybean trypsin inhibitor as ligand (CDI method). Sepharose CL-6B (1 g moist cake) was actived with CDI (0.15 g) and divided into two equal portions. Each was treated with soybean trypsin inhibitor (15 mg) in 1 ml buffer for two days at 4° C. Portion (i) was 1 M in sodium carbonate at pH 10. Portion (ii) was 1 M in N,N,N',N' tetramethylethylene diamine at pH 9. The materials were washed alternately five times with 0.1 M sodium bicarbonate and 0.1 M sodium acetate (pH 4) each containing 0.5 M salt.

(c) Soybean trypsin inhibitor attached via a leash (CDI method) 6-aminohexanoic acid-SEPHAROSE CL-6B was prepared as in example 9a (half scale) and was treated at room temperature for 24 hours at pH 4.7 with STI (15 mg) and CMC (0.12 g). The material was washed as in example 9b.

(d) Soybean trypsin inhibitor as ligand (CNBr method). SEPHAROSE CL-6B (1 g moist cake) was activated with cyanogen bromide. The material was divided into two equal portions and then treated with STI as in example 9b. Affinity chromatography was carried out on 0.4–1 ml samples packed into Pasteur pipettes. The equilibrating, loading and washing buffer was 0.05 M Tris (pH 8) and desorbtion was carried out with 3 mM HCl. All solutions contained 0.5 M NaCl. Loadings were 20 mg trypsin in 16 ml buffer for examples 9a, 9b and 9d and 10 mg in 8 ml for example 9c.

Trypsin was analysed directly by u.v. spectroscopy at 280 nm.

The affinity supports described above had the trypsin capacities indicated in Table 5. In control experiments, 6-aminohexanoic acid-SEPHAROSE (both CDI and cyanogen bromide methods) showed no affinity for trypsin. In all cases removal of unbound trypsin was complete (u.v. monitor at 280 nm) and the subsequent pH shift caused rapid elution of the bound trypsin.

The CDI-activated affinity columns all had high capacities for trypsin, well up to the standards required for good preparative procedure. The capacities of matrices III and V where STI was coupled directly to the CDI-activated matrix were somewhat lower than those of the corresponding columns IV and VI made by the cyanogen bromide method. However the lack of charged isourea groups introduced at the coupling stage with the new procedure is probably the most significant difference from the cyanogen bromide method. In fact the higher binding capacity of the cyanogen bromide product could be at least partly due to non-specific binding.

The trypsin capacities of columns I and II, Table 5 i.e. those on which the ligand was coupled to a 6-aminohexanoic acid spacer group, were equally impressive.

In addition CDI activation of polysaccharide matrices offers a method of insolubilising a variety of organic molecules which contain amino groups. Such products are of value in the preparation of insolubilised receptors for radioimmune assays, insolubilised enzymes and ion exchange groups linked directly or through leashes.

TABLE 5
CAPACITIES OF TRYPSIN AFFINITY SUPPORTS

| AFFINITY COLUMN | TRYPSIN CAPACITY OF COLUMN (examples 9a-9d)[1] | |
| --- | --- | --- |
| | Per ml | Per sample |
| I p-aminobenzamidine-SEPHAROSE, CDI method | 12.4, 12.4[1] | 12.2, 13.0[1] |
| II trypsin inhibitor-6-amino-hexanoic acid leash-SEPHAROSE, CDI method. | 3.6 | 6.4 |
| III trypsin inhibitor-SEPHAROSE, CDI method, pH 9 coupling | 2.4 | 1.0 |
| IV trypsin inhibitor-SEPHAROSE, CNBr method, pH 9 coupling | 3.8 | 2.62 |
| V trypsin inhibitor-SEPHAROSE, CDI method, pH 10 coupling | 5.5 | 2.10 |
| VI trypsin inhibitor-SEPHAROSE, CNBr method, pH 10 coupling | 8.9 | 6.42 |

[1]The two values were for 5 or 10 mg of p-aminobenzenamidine respectively.

10. USE OF ACTIVATED MATRIX TO IMMOBILISE BIOLOGICALLY ACTIVE COMPOUNDS

The examples described in Table 6 were chosen to demonstrate that biologically active molecules could be linked to a polysaccharide matrix by the CDI method under conditions which allowed retention of their activity (for example see (b), (c), and (g), in Table 6). Other examples should provide useful materials for radioimmunoassays and radio-receptor assays (see example (a), (f) and (g) in Table 6).

TABLE 6
Some Further Examples of Organic Molecules With Amino Groups Linked to Sepharose CL-6B With CDI[1]

| Protein | Coupling Yield (%) | Protein Concentration on the Insolubilised Support (μmoles/g) |
| --- | --- | --- |
| (a) sulphanilic acid-azo-bovalbumin | 90[2] | 1.5[3] |
| (b) bovine thyroglobulin[5] | 94[2] | 0.6[3] |
| (c) bovine thyroid stimulating hormone (TSH)[6] | 88[2] | 3.6[3] |
| (d) porcine insulin | 100[2] | 4.5[3] |
| (e) human immunoglobulin | 87[2] | 1.5[3] |
| (f) creatinine | — | 18[4] |
| (g) 3,3',5-thyronine[7] | 78[2] | 52[4] |

[1]Prepared using the same method as for soybean trypsin inhibitor, each sample was coupled to 2g of CDI-activated SEPHAROSE (moist cake weight) which had been reacted with 50mg of CDI at pH 8.5 (0.1M borate).
[2]Estimated by the decrease in optical density (at λmax of the sample) of the washings relative to the coupling reaction.
[3]Determined by amino acid analysis of a 0.6g sample which had been hydrolyzed with 6N HCl, 110°, 24h.
[4]Determined by N elemental analysis.
[5]Binds significant quantities of human thyroglobulin autoantibodies, in fact the binding capacity is identical to the corresponding CNBr activated matrix.
[6]Binds rabbit anti-bovine TSH antibodies, and 1ml of gel neutralised completely a 1:32 dilution of a standard antibody preparation.
[7]1ml of gel completely neutralised 1:100 dilution of a rabbit antithyronine antibody.

What we claim is:

1. A compound of the general formula III wherein MATRIX is a water and organic solvent insoluble radical selected from the group consisting of: agarose, starch, dextran, cellulose, regenerated cellulose, hydroxy $C_2$–$C_4$ alkylated cellulose and hydroxy $C_2$–$C_4$ lower alkylated regenerated cellulose; and Y is a member selected from the group consisting of imidazoyl, 1,2,4-triazoyl and 1,2,3-benzotriazoyl.

2. The compound according to claim 1 wherein MATRIX in formula III is cross-linked.

3. The compound according to claims 1 or 2, wherein Y is imidazoyl.

4. The compound according to claim 1 or 2 wherein MATRIX is agarose.

5. The compound according to claim 1 or 2 wherein MATRIX is cross-linked hydrozypropylated regenerated cellulose.

6. A process for the preparation of a compound of the general formula III wherein MATRIX is a water and organic solvent insoluble radical selected from the group consisting of: agarose, starch, dextran, cellulose, regenerated cellulose, hydroxy $C_2$–$C_4$ alkylated cellulose and hydroxy $C_2$–$C_4$ lower alkylated regenerated cellulose; and Y is a member selected from the group consisting of imidazoyl, 1,2,4-triazoyl and 1,2,3-benzotriazoyl which process comprises:

carbonylating MATRIX as defined above, in an organic solvent selected from the group consisting of dimethyl formamide, dioxan and acetone at a temperature of 0° C. to 80° C., the upper temperature limit being below the degradation temperature of MATRIX; with a carbonylating agent wherein Y is selected from the group consisting of a diimidazole, a 1,2,4-triazole or a 1,2,3-benzotriazole.

7. A process according to claim 6 in which said carbonylating agent is selected from the group consisting of N,N'-carbonyl diimidazole; N,N'-carbonyl di-1,2,3-benzotriazole; and N,N'-carbonyl di-1,2,4-triazole.

8. The process according to claim 6 wherein MATRIX is cross-linked.

9. The process according to one of claims 6 or 8 wherein said carbonylating agent is N,N'-carbonyl di-1,2,4-triazole and the reaction is conducted for at least 5 minutes.

10. The process according to one of claims 6 or 8 wherein the carbonylating agent is N,N'-carbonyl di-1,2,3-benzotriazole, and is conducted in dioxan for a period of 7 days.

11. The process according to one of claims 6 or 8 wherein the carbonylating agent is N,N'-carbonyl diimidazole and the reaction is conducted in dioxan solution for at least 5 minutes.

12. A process for the preparation of a compound of the general formula V:

MATRIX-O—C(=O)—NR⁵R⁶     V wherein MATRIX is a cross linked water and organic solvent insoluble radical selected from the group consisting of agarose, starch, dextran, cellulose, regenerated cellulose, hydroxy $C_2$-$C_4$ alkylated cellulose and hydroxy $C_2$-$C_4$ lower alkylated regerated cellulose, $R^5$ is selected from the group consisting of hydrogen, and an alkyl, and $R^6$ being selected from the group consisting of —$(CH_2)_n$ $NH_2$, and —$(CH_2)_n CO_2H$ wherein n is an integer of from 2 to 12, which process comprises reacting a compound of the formula

MATRIX-O—C(=O)—Y wherein MATRIX is defined as above and Y is a member selected from the group consisting of imidazoyl, 1,2,4-triazoyl and 1,2,3-benzotriazoyl with an amine of the general formula $NHR^5R^6$ wherein $R^5$ and $R^6$ are as defined above.

13. The process as claimed in claim 12 wherein when in the compound of formula V, $R^5$ or $R^6$ is —$(CH_2)_n COOH$, n being from 2 to 12 the product is further reacted with a primary or secondary amine.

14. The process as claimed in claim 12 wherein when, in the compound of Formula V, R $R^5$ or $R^6$ is —$(CH_2)_n NH_2$, n being from 2 to 12, the product is further reacted with a carboxylic acid.

15. A compound of the general formula V:

MATRIX-O—C(=O)—NR¹—R²     V wherein MATRIX is a cross linked water and organic solvent insoluble radical selected from the group consisting of agarose, starch, dextran, cellulose, regenerated cellulose, hydroxy $C_2$-$C_4$ alkylated cellulose and hydroxy $C_2$-$C_4$ lower alkylated regenerated cellulose, $R^1$ is selected from the group consisting of hydrogen, and an alkyl, and $R^2$ being selected from the group consisting of —$(CH_2)_n$ $NH_2$, and —$(CH_2)_n CO_2H$, wherein n is an integer of from 2 to 12.

* * * * *

UNITED STATES PATENT AND TRADEMARK OFFICE
CERTIFICATE OF CORRECTION

PATENT NO. : 4,224,439
DATED : September 23, 1980
INVENTOR(S) : John S. Ayers, et al.

It is certified that error appears in the above—identified patent and that said Letters Patent is hereby corrected as shown below:

On the title page, item (75) Inventors: should read

-- John S. Ayers; Geoffrey S. Bethell; William S. Hancock, Palmerston North; Milton T. W. Hearn; Dunedin North, all of New Zeland --.

Signed and Sealed this

Twenty-fifth Day of November 1980

[SEAL]

Attest:

SIDNEY A. DIAMOND

Attesting Officer

Commissioner of Patents and Trademarks